United States Patent
Naidu et al.

(10) Patent No.: US 8,639,007 B2
(45) Date of Patent: Jan. 28, 2014

(54) GENERATING TWO-DIMENSIONAL PROJECTION IMAGES FROM HELICAL DATA

(75) Inventors: Ram Naidu, Newton, MA (US); Sergey Simanovsky, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 144 days.

(21) Appl. No.: 13/393,046

(22) PCT Filed: Aug. 28, 2009

(86) PCT No.: PCT/US2009/055369
§ 371 (c)(1),
(2), (4) Date: Feb. 28, 2012

(87) PCT Pub. No.: WO2011/025494
PCT Pub. Date: Mar. 3, 2011

(65) Prior Publication Data
US 2012/0177273 A1    Jul. 12, 2012

(51) Int. Cl.
*G06K 9/00*    (2006.01)
*A61B 6/00*    (2006.01)

(52) U.S. Cl.
USPC .............................. 382/131; 382/274; 378/15

(58) Field of Classification Search
USPC ......... 382/100, 103, 128–134, 141, 154, 162, 382/168, 173, 181, 189–190, 203, 209, 219, 382/224, 254, 274, 276, 285–295, 305, 382/312; 378/4, 14, 21, 15
See application file for complete search history.

(56) References Cited

U.S. PATENT DOCUMENTS

| | | | | |
|---|---|---|---|---|
| 5,802,134 | A * | 9/1998 | Larson et al. | 378/4 |
| 5,881,122 | A * | 3/1999 | Crawford et al. | 378/4 |
| 8,009,890 | B2 * | 8/2011 | Nishide et al. | 382/131 |
| 8,031,830 | B2 * | 10/2011 | Nakanishi | 378/15 |

OTHER PUBLICATIONS

International Search Report cited in related application No: PCT/US2009/055369 dated Apr. 26, 2010.
Karbeyaz et al., "Variable Pitch Reconstruction Using John's Equation", IEEE Transactions on Medical Imaging, IEEE Service Center, Piscataway, NJ, US LNKD-DOI: 10.1109/TMI.2008.922689, vol. 27, No. 7, Jul. 1, 2008, pp. 897-906.
Kachelriess; et al., "Advanced Single-Slice Rebinning in Cone-Beam Spiral CT", Medical Physics, AIP, Melville, NY, US LNKD-DOI: 10.1118/1.598938, vol. 27, No. 4, Apr. 1, 2000, pp. 754-772.

* cited by examiner

*Primary Examiner* — Seyed Azarian
(74) *Attorney, Agent, or Firm* — Cooper Legal Group LLC

(57) ABSTRACT

Techniques and/or systems for generating a two-dimensional projection image of an object under examination from helical data are provided herein. An image plane and a distance, or height, of an examination line lying in a plane parallel to the image plane may be selected with or without user input. Using the selected image plane and examination line, data may be extracted from one or more views indicative of the object. The data that is extracted from the respective views is generally indicative of rays that traverse the examination line and have a trajectory that meets predetermined criteria. Using the extracted data from a plurality of views, one or more projection lines that are substantially parallel to a corresponding image slice are produced and a two-dimensional projection image is generated.

20 Claims, 6 Drawing Sheets

GENERATING TWO-DIMENSIONAL PROJECTION IMAGES FROM HELICAL DATA

BACKGROUND

The present application relates to the field of radiographic imaging. It finds particular application with computed tomography (CT) scanners. It also relates to medical, security, and other applications where generating a two-dimensional projection image from data acquired from a helically scanned object would be useful.

CT and other radiographic imaging systems are useful to provide information, or images, of interior aspects of an object under examination. Generally, the object is exposed to radiation, and a two-dimensional image and/or three-dimensional image is formed based upon the radiation absorbed by the interior aspects of the object, or rather an amount of radiation that is able to pass through the object. Typically, highly dense aspects of the object absorb more radiation than less dense aspects, and thus an aspect having a higher density, such as a bone or mass, for example, will be apparent when surrounded by less dense aspects, such as fat tissue or muscle.

A radiation device typically comprises a detector array and a radiation source. In some scanners, such as three-dimensional imaging scanners (e.g., CT scanners), for example, the detector array and radiation source are mounted on opposing sides of a rotating gantry that forms a ring, or donut, around the object under examination. In a conventional CT scanner, the rotating gantry (including the source and/or detector array) is rotated in a circle situated within an x,y plane about an axis extending the z-dimension (e.g., an "isocenter") during a scan of the object. The object is generally supported by a support article (e.g., a bed, conveyor belt) that runs parallel with and is in close spatial proximity to the mechanical center of rotation (e.g., the isocenter). As the rotating gantry is rotated, radiation is substantially continuously emitted from a focal spot of the radiation source. Radiation that traverses the object is detected by a detector array and is used to generate signals and/or data that are indicative of the object, or rather interior aspects of the object. From these signals and/or data, two dimensional and/or three dimensional (projection and/or rendered) images can be generated.

Several sub-categories of CT scanners have been developed over the years. One sub-category of CT scanner is commonly referred to as a "step-and-shoot" or "constant z-axis" (CZA) CT scanner if the radiation is emitted in the form of a fan beam or a "stationary cone beam" CT scanner if the radiation is emitted in the form of a cone beam. Herein this sub-category is referred to as a CZA scanner. In such scanners, the object remains at a constant z-position relative to the focal spot during the scan (e.g., the object is not translated along in the z-dimension with respect to the focal spot during the scan). To obtain multiple projections, multiple scans of the object can be performed, respective scans performed when the object is at different z-positions (e.g., different positions along the z-axis relative to the focal spot). That is, the object is placed at a first z-position, a first scan of the object is performed, the object is placed at a second z-position, a second scan of the object is performed, etc. It will be appreciated that a projection image, or tomogram, formed from the multiple projections can depict a larger portion of the object than a projection image formed from a single projection.

There are several features about CZA scanners that make them disadvantageous for some applications. Generally, to reconstruct a two-dimensional and/or a three-dimensional image of the object under examination, data from a plurality of projections are assembled. To obtain the data from multiple projections using a CZA scanner is time consuming because the object must be moved between scans. Therefore, for time-sensitive applications (e.g., high-throughput luggage security applications, medical applications where a patient is asked to hold his/her breath, etc.) CZA scanners are undesirable. Additionally, the object (e.g., a human patient) may be exposed to high levels of radiation because at respective z-positions, radiation is generally emitted for at least a one hundred eighty degree rotation about the object.

Another sub-category of CT scanners that has been developed is commonly referred to as a "constant-speed-helical" (CSH) CT scanner if the radiation is emitted in the form of a fan beam or a "helical cone beam" (HCB) CT scanner if the radiation is emitted in the form of a cone beam. In such a scanner, the object being scanned is translated in the z-dimension relative to the focal spot as the rotating gantry is rotated about the patient causing a helical, or spiral, scan of the object. Thus, multiple projections may be acquired from a single scan of the object. Data that is yielded from a helical scan may be referred to as helical data.

While CSH and HCB scanners may obtain multiple projections of an object more quickly (because a larger portion of an object can be scanned during a single scan) and may expose the object to less radiation than a CZA scanner that is performing multiple scans, producing images from a CSH and/or an HCB scanner may require more computational steps (e.g., interpolations) than would be required for producing images from a CZA scanner and/or may have a reduced image quality relative to projection images produced from a CZA scanner. This is because none of the scanning planes (defined as planes through which radiation travels between the radiation source and the detector that are perpendicular to the z-axis about which the rotating gantry rotates) are co-planar. Rather respective "projections" or "views" (defined as signals and/or data generated from radiation striking the detector array within a predetermined amount of time) depict a unique z-dimension of the object. Therefore, before the signals and/or data can be converted from projection space to image space, the data is interpolated using techniques known to those skilled in the art. For example, interpolation may comprise combining projections taken at equivalent "projection angles" (e.g., defined as the angular orientation of the focal spot in an x,y plane relative to the object) and at different "cone angles" (e.g., defined as the angular orientation in a y,z plane focal spot relative to the object). Because of the interpolation, images produced from CSH and HCB scanners may have a lower resolution and/or increased artifacts relative to images produced from CZA scanners.

To overcome some of the disadvantages of the CSH and HCB scanners, a technique taught in U.S. Pat. No. 5,802,134 to Larson et al. and commonly referred to nutated slice reconstruction (NSR) was developed. NSR is, in particular, used with data generated from HCB scanners and generally involves extracting parallel projections from views that are reconstructed into tilted slices (where a "slice" is defined as a set of projections that share a similar scanning plane). Respective slices are tilted at a constant angle with respect to the mechanical center of rotation but increase in cone angle. Thus, the slices can be said to be nutated with respect to each other.

While nutated slice reconstruction has proven useful for producing three-dimensional images, when producing two-dimensional projection images object distortions can appear. For example, straight edges in aspects of the object that are slanted with respect to the mechanical center of rotation may appear wavy. Such distortion may be undesirable because it may reduce image quality and/or interfere with threat detection in a security application, for example.

SUMMARY

Aspects of the present application address the above matters, and others. According to one aspect, a method is provided. The method comprises selecting first data from a first view indicative of an object under examination and yielded from a first ray. The method also comprises selecting second data from a second view indicative of the object under examination and yielded from a second ray. The method further comprises generating a two-dimensional projection image of the object using the selected first and second data.

According to another aspect, a method is provided. The method comprises extracting a first segment of data from a first view indicative of a helically scanned object and a second segment of data from a second view indicative of the object. The method also comprises using the first segment of data and the second segment of data to yield a two-dimensional projection image.

According to another aspect, a method is provided. The method comprises generating a projection line that is substantially parallel to an image slice of an object and is used to create a two-dimensional projection image of the object. The projection line is generated using data yielded from radiation that traversed one or more planes substantially passing through an examination line lying within a first plane that is parallel to an image plane within which the generated two-dimensional projection image lies. The one or more planes are substantially perpendicular to the examination line.

According to yet another aspect, an apparatus is provided. The apparatus comprises a data extraction component configured to extract a segment of data from each of a plurality of views of an object that is helically scanned. The apparatus also comprises an image reconstructor configured to reconstruct a two-dimensional projection image of the object, the two-dimensional projection image yielded from the extracted segments of data.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
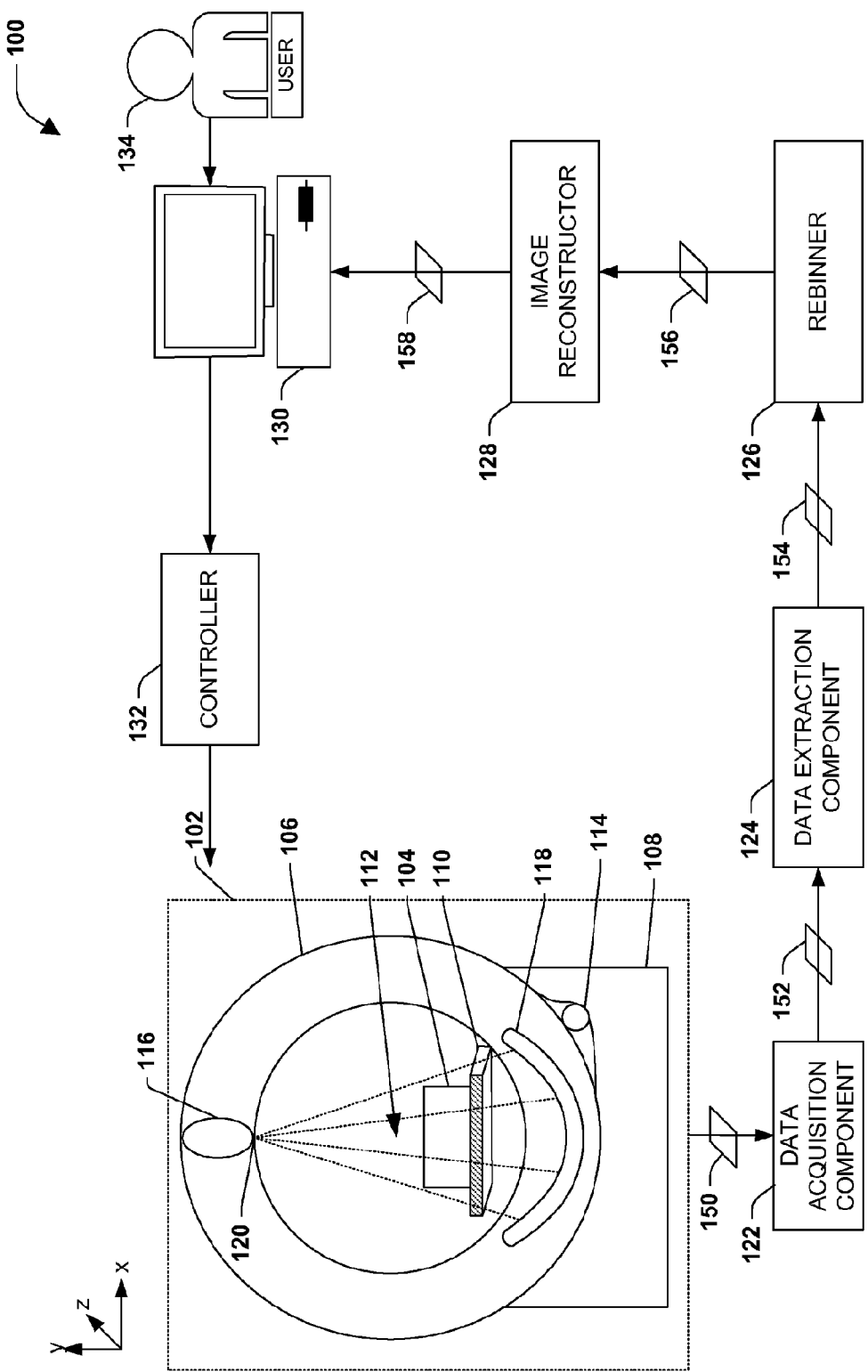
FIG. 1 is a schematic block diagram illustrating an example scanner.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Systems and techniques for generating two-dimension (2D) projection images of scanned objects from helical data (e.g., data generated by a CSH or HCB scanner) are provided herein. Using such systems and/or techniques, one or more 2D projection images with reduced distortion of edges (relative to the distortion caused by a projection image produced from NSR) and/or enhanced at a desired height relative to an image plane, or an examination surface of a support article, may be produced.

FIG. 1 is an illustration of an example environment 100 in which a two-dimensional projection image 158 of an object 104 that has been subjected to imaging using an imaging apparatus (e.g., a CT scanner) may be produced. Such a scanner may be used to identify a tumor in a human patient at a medical center and/or to identify potential threats at a security checkpoint, for example.

In the example environment 100, the imaging apparatus comprises an object scanning apparatus 102 configured to scan one or more objects 104 (e.g., a series of suitcases at the airport). The object scanning apparatus 102 typically comprises a disk-shaped rotating gantry 106 and a stationary gantry 108. During a scan of the object(s) 104, the object(s) 104 is placed on a examination surface (e.g., an x,z plane) of a support article 110, such as a bed or conveyor belt, that is selectively positioned in an examination region 112 (e.g., a hallow bore in the rotating gantry portion 106), and the rotating gantry 106 is rotated by a rotator 114 relative to the stationary gantry 108.

The disk-shaped rotating gantry 106 generally surrounds a portion of the examination region 112 and comprises a radiation source 116 (e.g., an ionizing x-ray source) and a detector array 118 that is mounted on a substantially diametrically opposite side of the rotating gantry 106 relative to the radiation source 116. The detector array 118 generally comprises one or more rows of detector elements (respective elements comprised of a plurality of pixels) that are generally, but not necessarily, disposed in the shape of an arc having a center of curvature at a spot 120, referred to as a "focal spot," where radiation is emitted from the radiation source 116. It will be appreciated that "row" is used herein to refer to a plurality of detector elements passing through a first plane (e.g., a x,y plane) that is parallel to a plane in which the rotating gantry rotates and "column" is used herein to refer to a plurality of detector elements passing through a second plane that is substantially perpendicular to the first plane (e.g., a y,z plane). In the example environment 100, a first row of detector elements (not shown) passes through a first x,y plane and a second row of detector elements (not shown) passes through a second x,y plane.

During a scan of the object 104, the radiation source 116 (which may be rotating along with the rotating gantry 106) emits radiation in the form of a fan beam and/or a cone beam onto the object 104 from the focal spot 120. It will be understood to those skilled in the art that the terms "fan beam" are used broadly herein to describe radiation that may be incident on the detector array 118 in the form of a one-dimensional projection, and the terms "cone beam" are used broadly herein to describe radiation that may be incident on the detector array 118 in the form of a two-dimensional projection. Generally, a plurality of rows of detector elements can detect radiation emitted in the form of a cone beam as compared to radiation emitted in the form of a fan beam which can, generally, be detected by only a single row of detector elements. In this way, radiation can traverse a larger z-dimension of the object 104 when radiation is emitted in the form of a cone beam than it can when it is emitted in the form of a fan beam. It will be appreciated that the terms cone beam and/or fan beam are not used herein to refer to a particular geometric shape of the radiation that is emitted. For example, the radiation may be conical, wedge-shaped, pyramidal, etc.

Figure 1B:
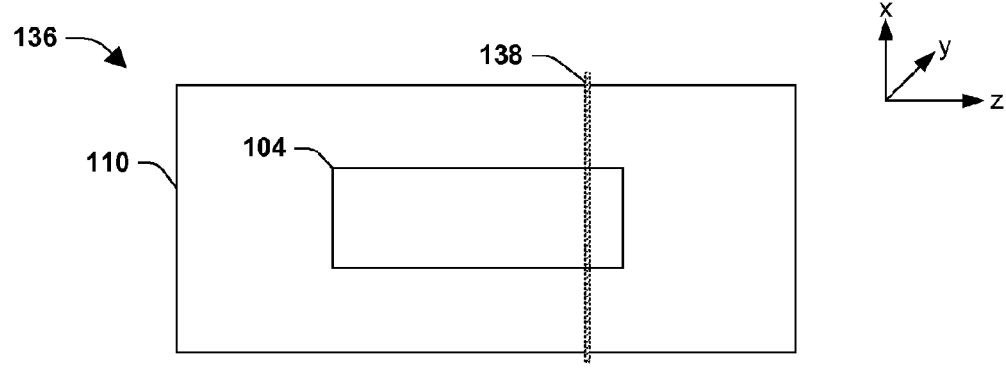
FIG. 1(b) illustrates a top-down view of an example fan beam.
Figure 1C:
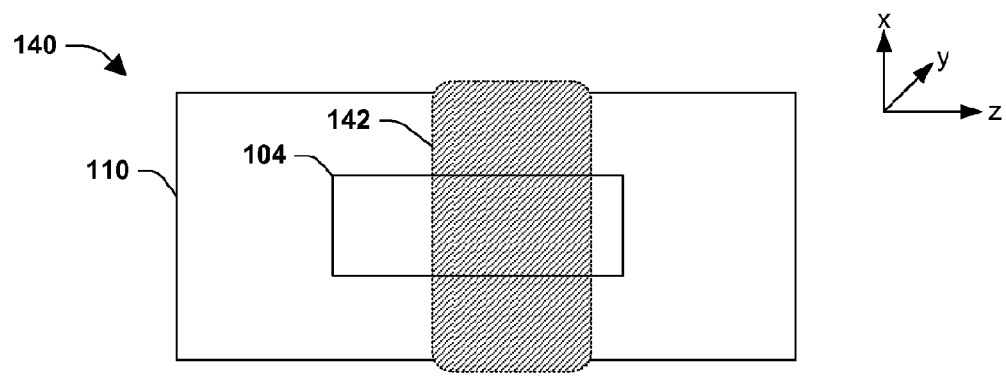
FIG. 1(c) illustrates a top-down view of an example cone beam

Nevertheless, by way of example and not limitation, FIG. 1b illustrates a top-down view 136 of an example fan beam 138, and FIG. 1c illustrates a top-down view 140 of an example cone beam 142, where "top-down" is a view in the y-direction from the radiation source 116 to the detector array 118. Accordingly, a cross-sectional view of the fan beam 138 near the support article 110 is illustrated in FIG. 1b, while a cross-sectional view of the cone beam 142 near the support article 110 is illustrated in FIG. 1c. To generate the fan beam 138, the focal spot 120 in the radiation source 116 is essentially opened very little. In the illustrated example, the focal spot 120 may comprise a slit through which radiation may escape. Thus, the cross-section of the fan beam 138 appears to have an x-dimension, but little to no z-dimension. To generate a cone beam 142, on the other hand, the focal spot 120 may be larger so that more radiation may escape the radiation source 116. Thus, the cross-section of the cone beam 142 appears to have both an x-dimension and z-dimension. A cone beam 142 can, in some respects, thus be thought of as comprising many adjacent fan beams. Nevertheless, these examples are not meant to be limiting.

Radiation that traverses the object 104 is detected by pixels of the detector array 118 (which may also be rotating along with the rotating gantry 106). Radiation that can be incident on a pixel at a measuring interval during a scan is commonly referred to as a "ray," and respective pixels generate an output signal 150 and/or output data indicative of the intensity of rays detected by the pixels (e.g., where intensity is indicative of the attenuation of the ray as it passed through the object 104). It will be appreciated that the measuring interval may be a predefined interval of time and may depend upon the time in which it takes a signal to return to a baseline (e.g., a threshold signal that is emitted when a ray is not detected by a pixel) and/or may be defined based upon the rotational speed of the rotating gantry 106, for example.

While the object 104 is being scanned, the object 104 may be translated along an axis traveling in the z-dimension (if, as illustrated, the rotating gantry 106 is configured to rotate in an x,y plane). In this way, an object that has a z-dimension greater than the z-dimension of the radiation traversing the object may be scanned more quickly (relative to a step-and-shoot scanning approach). It will be appreciated that if the object 104 is being translated during a scan while the rotating gantry 106 is rotating, the scan may be referred to as a helical or spiral scan. As a result of the helical scanning, two or more scanning planes may not be co-planer.

As an example, a computed tomography (CT) security scanner 100 that includes an x-ray source 116, such as an x-ray tube, can generate a cone-beam of x-ray radiation that traverses one or more objects 104, such as a suitcase, traveling from an upstream portion to a downstream portion of an examination region 112 (e.g., traveling into or out of the page). In this example, the x-rays that are emitted by the source 116 traverse the examination region 112 that contains the object(s) 104 to be scanned and are detected by an x-ray detector array 118 across from the x-ray source 116. Further a rotator 114, such as a gantry motor drive attached to a rotating gantry portion 106 can be used to rotate the x-ray source 116 and the detector array 118 around the object(s) 104 while the object is translated from an upstream portion of the examination region 112 to a downstream portion (e.g., moving the object out of the page), for example. Output signals 150 generated from pixels of the x-ray detector array 118 during a scan of the object(s) 104 and indicative of a spiral scan may be output from the object scanning apparatus 102.

It will be appreciated that in other embodiments, a three-dimensional object scanning apparatus may be configured differently than the object scanning apparatus 102 illustrated in the example environment 100 and described herein. For example, in another embodiment, the rotating gantry 106 is stationary and the object 104 is rotated in the examination region 112.

In the example environment 100, a data acquisition component 122 is operably coupled to the object scanning apparatus 102 and is configured to receive the output signals 150, output data, and/or other information from the detector array 118 or, more generally, the object scanning apparatus 102. Where the data acquisition component 122 receives output signals 150, the data acquisition component 122 may also be configured to filter the output signals 150 using filtering techniques commonly known to those skilled in the art to improve the signal-to-noise ratio of the output signals 150.

The data acquisition component 122 may also be configured to compile the output signals 150, output data, and/or other information that is received during a measuring interval (e.g., from the respective pixels) and generate projection space data 152. Such a compilation is commonly referred to as a "view" or a "projection." It will be appreciated that the terms "cone view" are used herein to refer to a view indicative of information generated by measuring radiation emitted in the form of a cone beam, and the terms "fan view" are used herein to refer to a view indicative of information generated from radiation emitted in the form of a fan beam.

Because the measuring interval corresponds to the orientation of the rotating gantry 106, a view may be said to represent information collected from radiation emitted while the focal spot 120 was at a particular x,y,z position, or more generally, at a particular range of x,y,z coordinates, relative to the object being scanned. Generally, if the object is being translated in the z-direction while the focal spot is rotated in an x,y plane, no two views represent information collected from radiation emitted while the focal spot was at the same position relative to the object.

In the example environment 100, the projection space data 152 indicative of a first view is transmitted to a data extraction component 124. The data extraction component 124 is configured to extract a segment of data from the first view. Determining which segment in the first view to extract may be based upon a desired image plane within which the two-dimensional projection image lies (e.g., the angle at which a person wishes to view the object) and/or an orientation of an examination line (e.g., an imaginary line chosen for enhancing or optimizing the projection image), which may be at least partially determined based upon the desired image plane, for example. In one example, a user may select to view a top-down image and an examination line extending in the x-direction may be generated because a top-down image was selected. The user can then adjust the y-position of the examination line to enhance the image, for example, while still viewing a top-down image of the object.

The data extracted may be yielded from a ray that follows a (desired) trajectory that passes through and is substantially perpendicular to an examination line lying within a first plane that is substantially parallel to the image plane within which the two-dimensional projection image lies and/or traverses a second plane perpendicular to the examination line, for example. In one example, where a top-down projection image is desired, the data that is extracted from the first view may be data indicative of a first ray. The first ray intersects an examination line extending in the x-dimension and lying in a first plane parallel to an image plane that extends in an x,z plane (e.g., because it is a top-down image). The first ray may also traverse a second plane that is perpendicular to the examination line. It will be appreciated that ordinarily, the examination line lies in a plane that is parallel to the plane within which the focal spot is rotated. For example, if the focal spot is rotated in an x,y plane, the examination line is positioned in an x,y plane.

In one embodiment, the data extraction component 124 calculates a "projection angle" (defined herein as the angle formed by a first and second line originating from the focal spot 120 and traversing an x,y plane through which the focal spot rotates; the first line intersecting the isocenter and the second line intersecting an image plane at a perpendicular angle) and a "cone angle" (defined as the angle formed by a third and fourth line originating from the focal spot 120 and traversing a first plane that is perpendicular to a second plane, parallel to the image plane, through which the examination line lies and perpendicular to the examination line; the third line intersecting the examination line and the fourth line intersecting the image plane at a perpendicular angle) of a ray meeting the above mentioned criteria (e.g., a desired trajectory). In the illustrated example, the first and second lines would traverse an x,y plane and, where a top-down image is desired (e.g., the examination line extends in the x direction), the third and fourth lines would traverse a y,z plane. (It will be appreciated that in one example, the second and fourth lines may actually correspond to the same line (e.g., a line starting at the source and running parallel to the y axis for a top-down view)). Using the projection angle and the cone angle, the data extraction component 124 may then determine where such a ray would intersect the detector array to determine which segment of data to extract.

It will be appreciated that the data extraction component 124 may also receive projection space data indicative of second, third, fourth, etc. views and may be configured to extract a segment of data from the respective, second, third, etc. views. Determining which segments in the second, third, etc. views may also be based upon the desired image plane and/or the examination line (e.g., so that parallel projections may be produced and a two-dimensional image can be generated).

FIGS. 2-4 illustrate rays that may respectively yield a segment of data to be extracted by a data acquisition component (e.g., 124 in FIG. 1) for respective views when a top-down image (e.g., an image lying in an x,z image plane 218) is desired. By determining the location on a detector array 202 where respective rays would have been detected, the data extraction component may determine which segment of data to extract from each of the plurality of views.

FIGS. 2-4, respectively, illustrate the detector array 202 (e.g., 118 in FIG. 1), a focal spot 204 (e.g., 120 in FIG. 1) of a radiation source (e.g., 116 in FIG. 1), an isocenter 206 about which a rotating gantry (e.g., 106 in FIG. 1) rotates, and a support article 210 (e.g., 110 in FIG. 1), of an object scanning apparatus (e.g., 102 in FIG. 1). FIGS. 2-4 also illustrate an object 214, an examination line 212 (e.g., an imaginary line chosen for enhancing or optimizing the image), and an image plane 218 (e.g., parallel to an x,z plane).

Figure 2A:
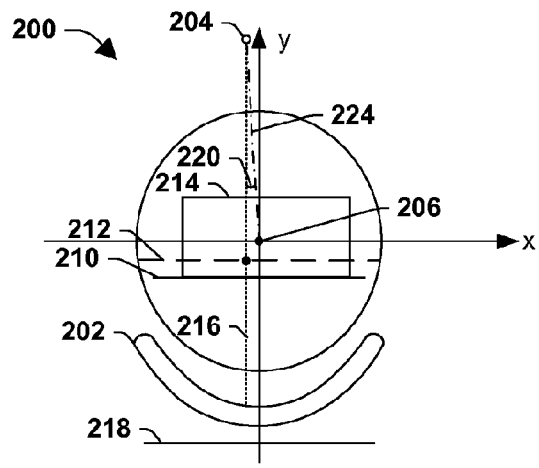
FIG. 2(a) illustrates a side view of a scanner and of a ray that may yield a segment of data to be extracted from a first view indicative of an object under examination.
Figure 2B:
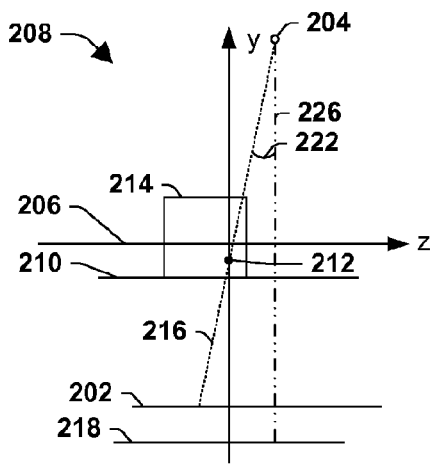
FIG. 2(b) illustrates a view looking into a scanner of a ray that may yield a segment of data to be extracted from a first view indicative of an object under examination.
Figure 3A:
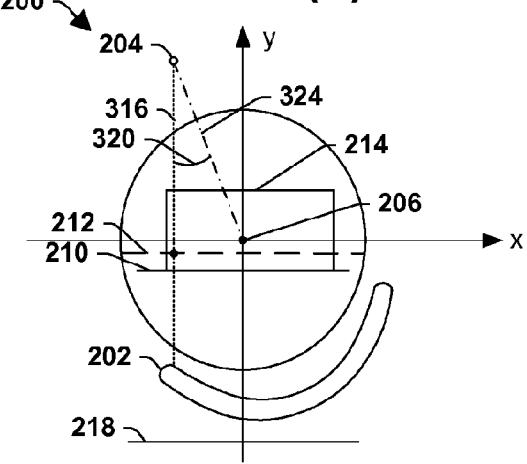
FIG. 3(a) illustrates a side view of a scanner and of a ray that may yield a segment of data to be extracted from a second view indicative of an object under examination.
Figure 3B:
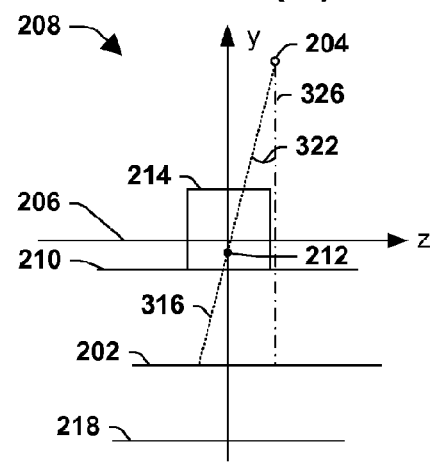
FIG. 3(b) illustrates a view looking into a scanner of a ray that may yield a segment of data to be extracted from a second view indicative of an object under examination.
Figure 4A:
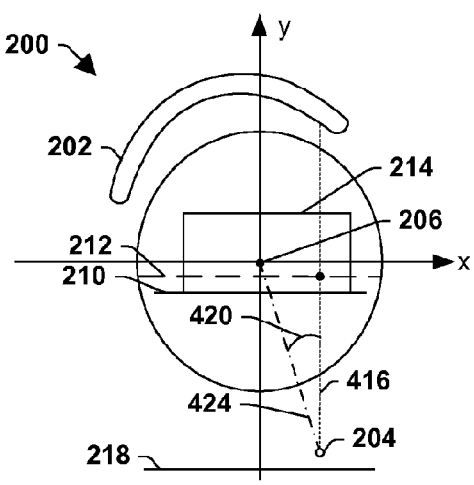
FIG. 4(a) illustrates a side view of a scanner and of a ray that may yield a segment of data to be extracted from a third view indicative of an object under examination.
Figure 4B:
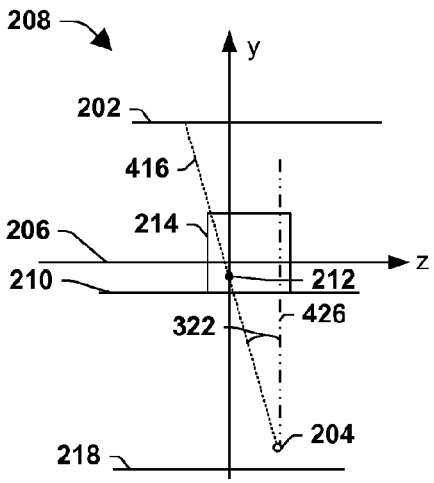
FIG. 4(b) illustrates a view looking into a scanner of a ray that may yield a segment of data to be extracted from a third view indicative of an object under examination.

It will be appreciated that FIGS. 2(a), 3(a), and 4(a) (the "(a)" Figs.) further illustrate a cross-section of the object scanning apparatus through a first plane that is parallel to a second plane through which the focal spot 204 (and rotating gantry) rotates (e.g., an x,y plane). In the (a) Figs., the object 214 would be going into or out of the page if it was being translated in the z-dimension. FIGS. 2(b), 3(b), and 4(b) (the "(b)" Figs.) illustrate a cross-section of the object scanning apparatus through a plane that is perpendicular to the image plane 218 and perpendicular to the examination line 212 (e.g., a y,z plane). In the (b) Figs., the object 214 would be going left or right on the page if it was being translated in the z-dimension. Thus, aspects may appear differently in the (a) Figs. than they do in the (b) Figs. For example, the z-axis, which passes through the isocenter 206, appears as a point in the (a) Figs. and as a line in the (b) Figs. Similarly, the examination line 212 (which extends in the x-dimension when producing a top-down image) appears as a (dashed) line in the (a) Figs. and as a point in the (b) Figs.

It will also be appreciated that while an object 214 appears to remain in the same position from the perspectives depicted in the (a) Figs (e.g. the x,y orientation of the object does not change), as illustrated in the (b) Figs. the object 214 is being translated along the z-axis relative to the focal spot.

The focal spot 204 emits radiation in a plurality of directions in the form of a fan beam or a cone beam. In FIGS. 2-4, the radiation is emitted in the form of a cone beam (e.g., the radiation extends in the z-dimension away from the z-position of the focal spot). However, the systems and/or techniques described herein may also be applied when radiation is emitted in the form of a fan beam.

FIGS. 2(a) and 2(b) illustrate a first ray 216 that would yield data comprised within a first cone view. The first ray 216 follows a trajectory that passes through and is perpendicular to the examination line 212 (extending in the x-dimension) that lies in a first plane perpendicular to the image plane (e.g., an x,z plane). The first ray 216 also traverses a second plane perpendicular to the examination line (e.g., a y,z plane).

Data yielded from the first ray 216 may be extracted from the first cone view to generate a top-down projection image. Recall that the first cone view would generally comprise data yielded from radiation emitted while the focal spot 204 was at a first x,y,z position relative to the object. For a top-down image, the examination line 212 may extend in the x-dimension at a given, or predetermined, y-dimension.

A data acquisition component comprises information (e.g., the speed of rotation, the speed at which the object 214 is translated, etc.) that allows the data acquisition component to calculate the orientation of the focal spot relative to the object. From such information, a projection angle 220 (measured as the angle between the first ray 216 and a dash-dot line 224) and a cone angle 222 (measured as the angle between the first ray 216 and the dash-dot-dot line 226) that would cause a ray to follow the desired trajectory (e.g., the trajectory followed by the first ray 216) can be calculated. It will be appreciated that where radiation is emitted in the form of a fan beam, the cone angle 222 may be substantially zero.

In FIGS. 3(a) and 3(b) the focal spot 204 is at a second x,y,z position with respect to the object 214. Stated differently, the rotating gantry (including the focal spot 204 and the detector array 202) have rotated in the x,y plane, and the object 214 has been translated in the z-dimension to a z-position nearer the focal spot 204 relative to the z-position of the object 214 depicted in FIG. 2(b). Radiation emitted while the focal spot 204 is at the second position and detected by the detector array 202 may be used to generate a second cone view that is different than the first cone view. Generally, the examination line 212 remains in the same orientation during the scan (e.g., the orientation of the examination line 212 is the same in FIGS. 2-4).

FIGS. 3(a) and 3(b) illustrate a second ray 316, different than the first ray 216, which would yield data comprised within the second cone view. Similar to the first ray 216, the second ray 316 follows a trajectory that passes through and is perpendicular to the examination line 212 that lies in the first plane perpendicular to the image plane 218. The second ray 316 also traverses a third plane perpendicular to the examination line.

To determine which data of the second cone view to extract, the data acquisition component may determine the projection angle 320 (measured as the angle between the second ray 316 and the dash-dot line 324) and the cone angle 322 (measured as the angle between the second ray 316 and the dash-dot-dot line 326) of a ray that would follow the desired trajectory (e.g., the trajectory of the second ray 316). The data acquisition component may then identify the location on the detector array 202 where the second ray 316 would be detected and extract data yielded from the second ray 316.

In FIGS. 4(a) and 4(b) the focal spot 204 is at a third x,y,z position with respect to the object 214. The third x,y,z position is different than the first x,y,z position illustrated in FIG. 2 and the second x,y,z position illustrated in FIG. 3. Radiation emitted while the focal spot 204 is at the third position and detected by the detector array 202 may be used to generate a third cone view that is different that the first or second cone views.

FIGS. 4(a) and 4(b) illustrate a third ray 416, different than the first ray 216 and/or the second ray 316, which would yield data comprised within the third cone view. Similar to the first ray 216 and the second ray 316, the third ray 416 follows a trajectory that passes through and is perpendicular to the examination line 212 that lies in the first plane perpendicular to the image plane 218. The third ray 416 also traverses a fourth plane perpendicular to the examination line.

To determine which data of the third cone view to extract, the data acquisition component may determine the projection angle 420 (measured as the angle between the third ray 416 and the dash-dot line 424) and the cone angle 422 (measured as the angle between the third ray 416 and the dash-dot-dot line 426) of a ray that would follow the desired trajectory (e.g., the trajectory of the third ray 416). That data acquisition component may then identify the location on the detector array 202 where the third ray 416 would be detected and extract data yielded from the third ray 416.

Returning to FIG. 1, in the illustrated environment 100, the data extraction component 124 is also operably coupled to a terminal 130 that may be configured to receive user input from a user 134. In this way, the user 134 can determine an orientation of the examination line (and thus determine from which angle to view the object) and/or determine from which angle to view the object (and thus at least partially determine the orientation of the examination line). For example, a default orientation may cause a top-down image of the object to be displayed on a monitor of the terminal 130, and a user may select a side-view of the object (e.g., causing the examination line to change orientation from a first orientation in which the examination line extended in the x-dimension to a second orientation in which the examination line extends in the y-dimension). It will be appreciated that in some embodiments, such as where a user 134 can alter the orientation of the examination line after a first image depicting the object 104 from a first angle is produced, the data extraction component 124 may be configured to store the projection space data 152 and/or may be operably coupled to a storage medium configured to store the projection space data 152. In this way, segments can be extracted from the respective cone views after an initial image is generated, for example.

In the example environment 100, extracted projection space data 154 output from the data extraction component 124 is transmitted to a rebinner 126 configured to receive extracted projection space data 154 that was extracted from the first view (and projection space data extracted from a plurality of other views). In one embodiment, the rebinner is configured to interpolate the extracted data to identify, or generate, data indicative of the desired ray. Stated differently, the data extraction component 124 may extract more data than just the data yielded from a single ray (e.g., because no actual ray followed the trajectory of the desired ray, the desired ray intersected a gap between two or more pixels, etc.), and the rebinner 126 may interpolate the extracted projection data from the first view to generate (only) data that would have been generated by the desired ray intersecting (only) one pixel of the detector array 118. For example, the data extraction component 124 may extract data yielded from four pixels that are in a close spatial proximity to a location where the desired ray would have intersected the detector array 118, and the rebinner 126 may interpolate the data using techniques known to those skilled in the art to generate (a close approximation to) the data that would have been yielded from the desired ray.

The rebinner 126 may also be configured to use the data that would have been yielded from the desired ray, along with data from a plurality of other views that would have been yielded from desired rays, to generate a projection line, or virtual view 156, indicative of an image slice (e.g., indicative of a portion of the image). It will be appreciated that the projection line is substantially parallel to a slice plane of the image slice.

Figure 5:
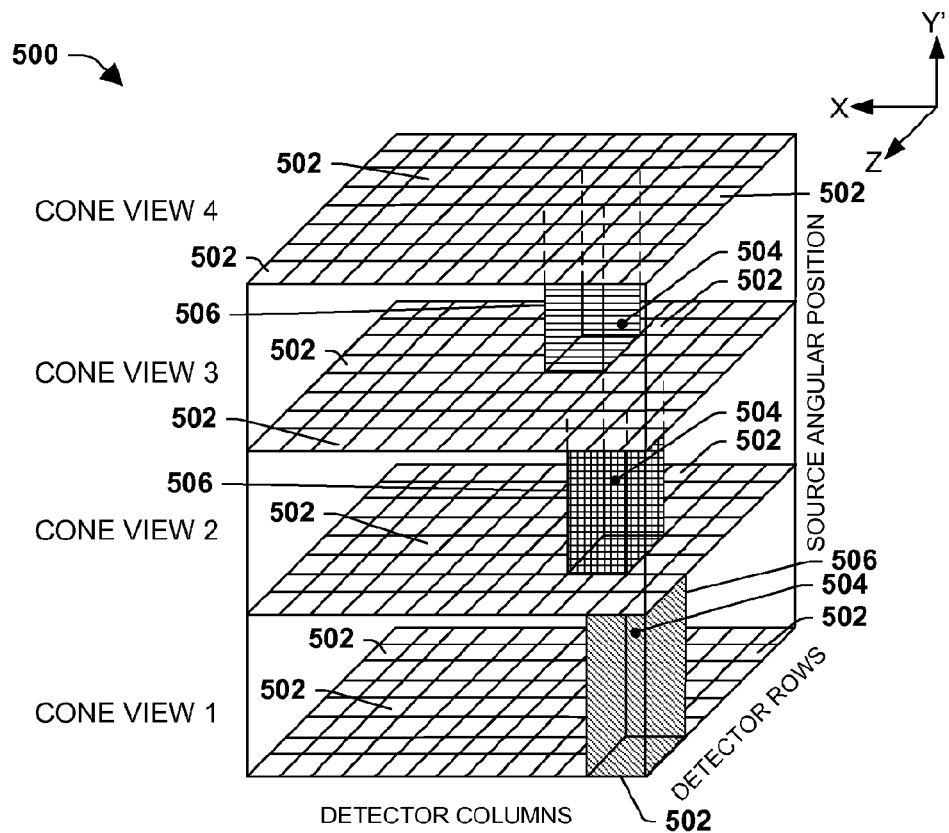
FIG. 5 illustrates segments of data that are extracted from respective cone views.
Figure 6:
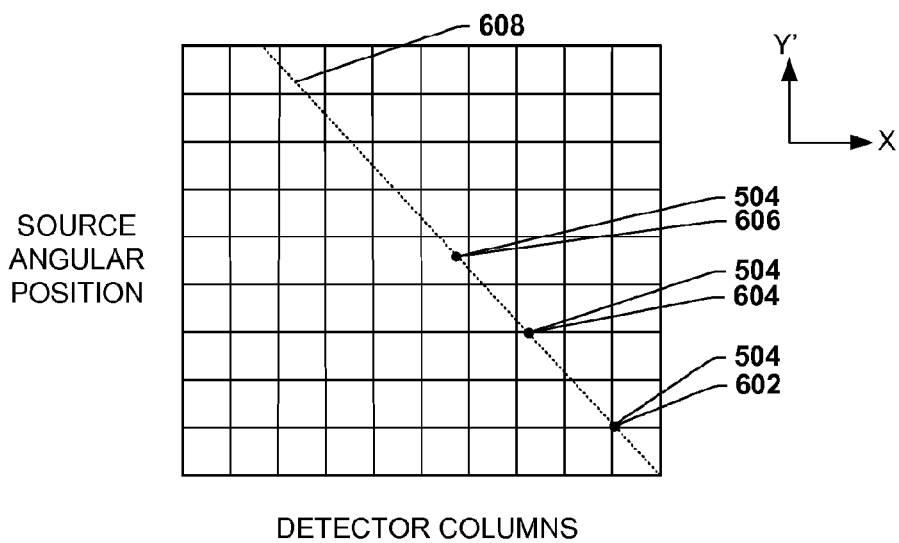
FIG. 6 illustrates extracted segments of data being used to generate a projection line.

FIGS. 5-6 illustrate a graphical representation of extracted projection data from a plurality of views 500 and of the interpolation that a rebinner (e.g., 126 in FIG. 1) may perform on the extracted projection data (e.g., 154 in FIG. 1) to generate the data that would have been yielded from the desired ray. Further, FIG. 6 illustrates the data extracted from a plurality of views being used to generate a projection line, or virtual view 156.

More particularly, FIG. 5 illustrates a plurality of cone views 500 from which a data extraction component may extract segments of data. As illustrated, respective cone views 500 comprises data yielded from a plurality of pixels 502 (e.g., represented by small squares in the cone views 500) of a detector array. Respective pixels of each cone view may be said to be oriented in a particular detector column (wherein a column extends in a plane perpendicular to a plane through which a focal spot rotates) and a particular detector row (e.g., wherein a row extended in a plane parallel to a plane through which a focal spot rotates). In the illustrated example, the detector rows extend through respective x,y' planes and detector columns extend through respective y',z planes.

Because radiation is being emitted in the form of a cone beam, respective pixels may also comprise radiation collected while the object has a particular source angular position, or cone angle, with respect to the focal spot. It will be appreciated that because the object is substantially continuously translated along a z-axis, for example, and a view represents data collected during a measuring interval (generally greater than an instant of time), in practice pixels generally represent radiation collected over a particular source angular range. In the illustrated example, the range of the extracted data 506 is depicted on a y' axis (non-extracted data would have similar source angular range, but the range is not depicted in FIG. 5). It will also be appreciated that the source angular position is generally not the same as a change in a distance (e.g., height) between the object and the focal spot.

The data extraction component is configured to extract a segment of data generated from radiation detected by at least one pixel from the respective cone views 500. In one embodiment, because no ray that was detected followed a desired trajectory and/or because one view represents data from radiation detected during a measuring interval (which may be more than an instant of time), for example, data generated by more than one pixel is extracted. In the illustrated example, the data extraction component is configured to extract data 506 yielded from four pixels positioned in close spatial proximity to a point on the detector array where a desired ray (a ray that followed a desired trajectory) would have intersected the detector array. In the illustrated example, a dot 504 represents the desired data from the respective cone views 500 (e.g., the data that is indicative of a desired ray for that cone view).

When the data extraction component extracts data from the cone views 500 that is not desirable (e.g., data that is not indicative of a desired ray for that cone view), a rebinner may interpolate the extracted data 506 to generate data that is (only) indicative of the desired ray for that cone view. For example, if the rebinner receives extracted data from a cone view, the rebinner may perform an interpolation in the direction of the detector columns (e.g., reducing the x-dimension of the extracted data), an interpolation in the direction of the detector rows (e.g., reducing the z-dimension of the extracted data), and an interpolation along the source angular position (e.g., reducing the y'-dimension of the extracted data) to generate data that is (only) indicative of the desired ray. It will be appreciated that where the extracted data is from a fan view, the rebinner may not perform an interpolation along the source angular position because the extracted data 506 would be two-dimensional.

FIG. 6 illustrates the data from the respective cone views 500 after the rebinner has performed interpolation on the extracted data 506. For example, first data 602 may be yielded (after interpolation) from extracted data 506 of the first cone view, second data 604 may be yielded (after interpolation) from the extracted data 506 of the second cone view, and third data 606 may be yielded (after interpolation) from the extracted data 506 of a third cone view. Using the first 602, second 604, and third 606 data, the rebinner can generate a first projection line 608, or virtual view (e.g., 156 in FIG. 1), at a substantially similar location as an image slice of an object being scanned. The rebinner may repeat the acts of interpolating data from a plurality of cone views and generate a plurality of projection lines, or virtual views; the plurality of projection lines indicative of a respective image slice and parallel to the image slice.

Returning to FIG. 1, in the example environment 100, the virtual view 156 is transmitted to an image reconstructor 128 configured to receive the virtual view 156. The image reconstructor 128 is also configured to combine the virtual view 156 with a plurality of other virtual views to generate one or more two-dimensional projection images 158 of the object 104 under examination using analytic, iterative, or other image reconstruction techniques known to those skilled in the art (e.g., 2D filtered back projection). That is, a plurality of projection lines generated by the rebinner 126 and, respectively, indicative of an image slice are converted from projection space to image space.

The example environment 100 also includes a terminal 130 (e.g., a computer) configured to receive the 2D projection image 158. The 2D projection image 158 may be displayed on a monitor of the terminal 130 to a user 134 (e.g., security personnel, medical personnel, etc.). In this way, a user can inspect the image 158 to identify areas of interest within the object 104.

The terminal 130 may also be configured to receive user input which may direct the object scanning apparatus 102 how to operate (e.g., a speed to rotate, a speed of a conveyor belt, etc.) and/or may be used by the data extraction component 124 to determine the orientation of the examination line and/or the image plane, for example.

In the example environment 100, a controller 132 is operably coupled to the terminal 130. The controller 132 may receive user input from the terminal 130 and generate instructions for the object scanning apparatus 102 indicative of operations to be performed. For example, the user 134 may want to rescan the object 104, and the controller 132 may issue an instruction instructing the support article 110 to reverse direction (e.g., bringing the object back into an examination region 112 of the object scanning apparatus 102).

Figure 7:
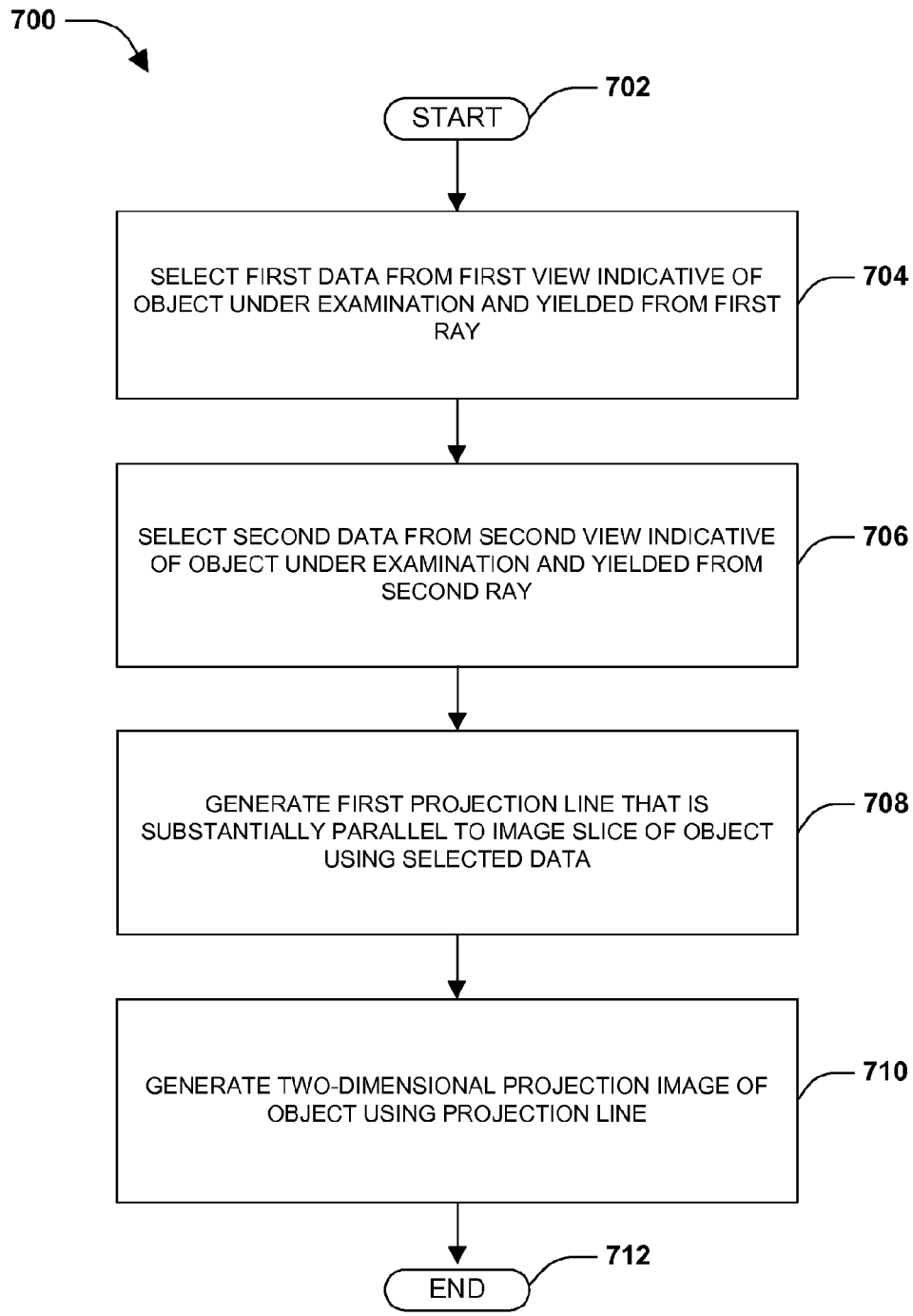
FIG. 7 is a flow diagram illustrating an example method of generating a two-dimensional projection image.

FIG. 7 illustrates an example method 700. Such a method 700 may be used to generate a two-dimensional projection image and/or a three-dimensional image from data generated during a helical scan of an object. A two-dimensional projection image produced from such a method may have an improved image quality relative to two-dimensional projection images produced by techniques known to those skilled in the art (e.g., nutated slice reconstruction). For example, aspects of an object that are slanted with respect to a z-axis along which the object is translated may appear to have straight edges instead of wavy edges that may appear in two-dimensional projection images produced by nutated slice reconstruction.

The example method 700 begins at 702, and first data (e.g., a first segment of data) from a first view indicative of an object under examination (e.g., an object being helically scanned) and yielded from a first ray is selected, or extracted, from the first view, at 704. At 706, second data (e.g., a second segment of data) from a second view indicative of the object under examination and yielded from a second ray is selected, or extracted, from the second view.

A view comprises data indicative of radiation that is incident on a detector array during a measuring interval (e.g., a predetermined range of time). For example, the first view may be indicative of radiation that was incident on the detector array during a first time interval (e.g., the first fifty milliseconds of a helical scan), and the second view may be indicative of radiation that was incident on the detector array during a second time interval (e.g., the next fifty milliseconds of the helical scan). In this way, a plurality of views indicative of the object under examination may be generated. It will be appreciated that the views may be cone views (e.g., produced from radiation emitted in the form of a cone beam) and/or fan views (e.g., produced from radiation emitted in the form of a fan beam).

The selected first and second data are yielded from a first ray and a second ray, respectively. A "ray" may be defined broadly as radiation that may be incident on a (single) pixel of a detector array. Generally, radiation is comprised of a plurality of rays. Determining which data to extract from the first and second views (and therefore which rays yield the data to be extracted) may be a function of predetermined criteria. In one embodiment, the data that is extracted is yielded from real or imaginary rays that follow a predetermined trajectory which passes through and is perpendicular to an examination line (an imaginary line used for generating and/or enhancing the projection image) lying within the plane. Further, the rays that yield the data that is to be extracted may traverse planes that are perpendicular to the examination line. That is, the first ray may traverse a first plane that is perpendicular to the examination line and a second ray may traverse a second plane that is perpendicular to the examination line. It will be appreciated that because a focal spot (emitting the radiation) is rotating about the object (e.g., in an x,y plane) and the object is being translated along an axis (e.g., extending in the z-dimension), a plurality of rays, emitted at different times and represented in different views, may meet the criteria listed above.

For example, where the desired two-dimensional projection image is a top-down image (looking down onto the object from above a support article on which the object resides), the image plane may be parallel to an examination surface of a support article upon which the object resides during an examination (e.g., the image plane may be lying in a first x,z plane), and the examination line may extend in the x-dimension through a second x,z plane. Data comprised within a first view and yielded from a first ray meeting the predetermined criteria may be extracted from the first view; data comprised within a second view and yielded from a second ray meeting the predetermined criteria may be extracted from the second view.

It will be appreciated that in some embodiments, data that is selected may comprise data that is generated from rays not meeting the predetermined criteria and interpolation techniques known to those skilled in the art may be applied to the data to generate data that would have been generated (only) from rays meeting the predetermined criteria. For example, where no ray actually follows the desired trajectory, data generated from pixels that detected rays that were in close spatial proximity (e.g., traveled a trajectory spatially similar to the desired trajectory) may be extracted, and interpolation may be performed on the extracted data to yielded data indicative of the first ray and the second ray respectively. Similarly, where a ray following the desired trajectory would have impinged the detector array near the edge of a pixel (e.g., causing the radiation's energy to be detected by a plurality of pixels), for example, data generated by a plurality of pixels may be selected, or extracted, from a view. In one example, data generated by four pixels that are in close proximity to (and including) the pixel that would have detected a ray meeting the predetermined criteria may be extracted from a view. Thus, it may be said that a first segment of data from a first view (indicative of a plurality of rays) is interpolated to generate first interpolated data (indicative of a single ray meeting the predetermined criteria) and a second segment of data from a second view (indicative of a plurality of rays) is interpolated to generate second interpolated data (indicative of a single ray meeting the predetermined criteria).

An examination line may provide a reference from which to enhance, or optimize, the image. Stated differently, an examination line may be a geometric reference line to determine which data to extract from a plurality of views. By keeping the examination line in substantially the same orientation while selecting, or extracting, data from a plurality of views, a two-dimensional projection image that is produced from the extracted data may be said to be enhanced, or optimized, with respect to the examination line.

In one embodiment, the orientation of the examination line may be (at least partially) selectively adjustable. For example, where a top-down image (lying in an x,z image plane) is to be produced, the direction along which the examination line extends can be based upon the orientation of the image (e.g., the examination line may extend in the x-direction and lie in an x,z plane), but the distance, or height, between the plane within which the examination line lies and the image plane may be selectively adjustable. Stated differently, the dimensions of a plane in which the examination line lies may be a function of the dimensions of a selected image plane (e.g., so the plane and the image plane are in parallel), but the distance between the planes may be adjustable. In one example, a user of a CT scanner may select the image plane (e.g., causing the dimensions of a plane in which the examination line lies to be determined) and the height of the examination line relative to the image plane. In this way, the image may be enhanced, or optimized, relative to a plane not intersecting the isocenter, for example.

It will be understood to those skilled in the art that being able to selectively adjust the orientation of the examination line may be especially useful for applications where the size and/or orientation of objects that are scanned is not uniform, such as airport luggage scanners, for example. In one embodiment, the examination line is adjusted based upon the object being scanned. For example, where top-down images are being generated, the examination line may be adjusted based upon the height of the object (e.g., the y-dimension of the object in FIG. 1) being scanned. An examination line may have a first height when a first object is scanned and may be (automatically) adjusted to a second height when a second, taller object is scanned.

It will be appreciated that the orientation of the image plane and/or the orientation (including height) of the examination line may be adjusted between objects and/or between two or more images of the same object. For example, a user may first select to view an object under examination from a top-down perspective in a first image and then select to view the object from the perspective of a side of the object in a second image. Similarly, the orientation may be automatically selected by the scanner based upon the dimensions of the object (e.g., a side view when a tall object is being scanned and a top-down view when a shorter object is being scanned). It will be appreciated that where two or more images of the same object are generated, two or more (non-overlapping or overlapping) segments of data from respective views that are used to generate the images may be extracted. For example, a first segment of data from a first view and a first segment of data from a second view may be used to produce a first image of the object, and a second segment of data from the first view and a second segment of data from the second view may be used to produce a second image of the object.

At 708, a first projection line that is substantially parallel to an image slice of the object under examination is generated using the selected data. That is, a projection line is formed based upon the selected data using analytic, iterative, or other techniques known to those skilled in the art. In this way, a virtual view of the object under examination may be generated. It will be appreciated that an image slice comprises data indicative of a portion of the object (e.g., imagine a loaf of bread sliced into a plurality of slices) and the first projection line is indicative of (e.g., represents) a first image slice (e.g., a first slice of bread).

Image slices are generally perpendicular to the axis through which the object is translated and the first projection line is substantially parallel to the image slice (e.g., the projection line is in a first plane that is parallel to a second plane in which the image slice lies). It will be appreciated that while the projection line is discussed herein as being generated using the first and second data, it will be appreciated that data selected from other views may also be used to generate the first projection line.

Generally, to generate a two-dimensional image of an object, a plurality of projection lines (respectively corresponding to a (unique) image slice) that are parallel to one another are generated and used to generate a two-dimension projection image through reconstruction techniques known to those skilled in the art. Thus, the acts described herein may be used to generate a plurality of projection lines that correspond to respective image slices. For example, a second projection line may be generated using third data, selected from a third view indicative of the object under examination and yielded from a third ray, and fourth data, selected from a fourth view indicative of the object under examination and yielded from a fourth ray. In this way, a plurality of projection lines that are substantially parallel to one another and represents different portions of the object (e.g., different image slices) may be generated.

At 712, a two-dimensional projection image of an object is generated using one or more projection lines, or, more broadly, using the selected data from the respective views. That is, projection lines, in projection space, are combined, for example, and converted to a projection image in image space using reconstruction techniques known to those skilled in the art (e.g., 2D filtered back projection).

The method 700 ends at 714.

Figure 8:
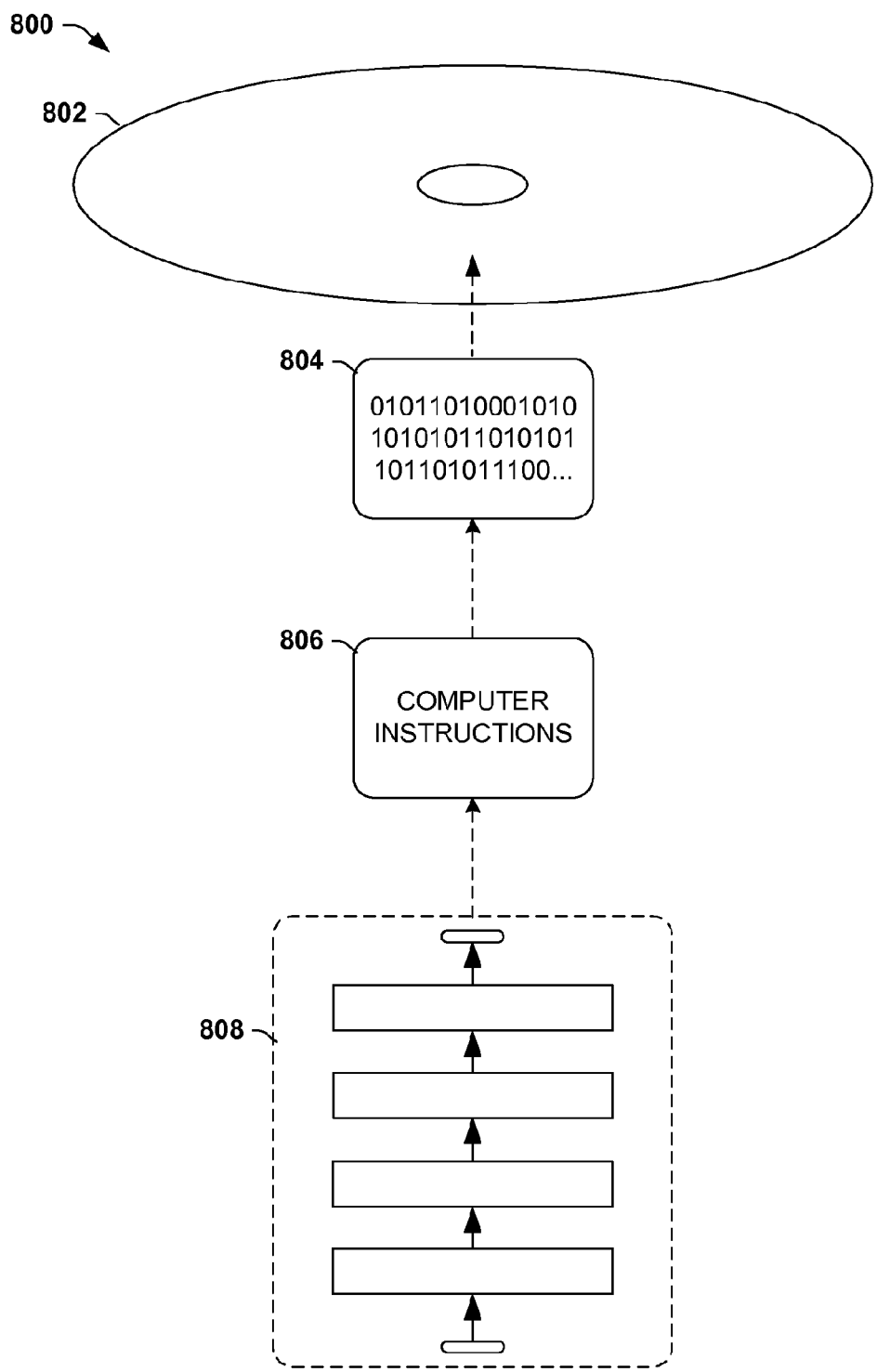
FIG. 8 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 8, wherein the implementation 800 comprises a computer-readable medium 802 (e.g., a CD-R, DVD-R, or a platter of a hard disk drive), on which is encoded computer-readable data 804. This computer-readable data 804 in turn comprises a set of computer instructions 806 configured to operate according to one or more of the principles set forth herein. In one such embodiment 800, the processor-executable instructions 806 may be configured to perform a method 808, such as the example method 700 of FIG. 7, for example. In another such embodiment, the processor-executable instructions 806 may be configured to implement a system, such as at least some of the exemplary scanner 100 of FIG. 1, for example. Many such computer-readable media may be devised by those of ordinary skill in the art that are configured to operate in accordance with one or more of the techniques presented herein.

It will be appreciated that there are numerous benefits to the systems and/or techniques described herein. For example, a two-dimensional projection image that is a closer approximation to a parallel projection produced by a line scanner (e.g., a scanner where the focal spot is not rotating with respect to the object) and/or a CZA scanner may be generated (relative to the two-dimensional projection images presently generated by helical scanners). Further, because the orientation of the examination line, or height of the examination line relative to the image plane, is selectively adjustable, the techniques and/or systems describes herein may be implemented on scanners already in use (e.g., the techniques and/or systems are portable across scanner designs). Similarly, the extraction of segments is dependent on the image plane (and/or orientation of the examination line), and thus the image may have a higher resolution and/or aspects of the object may be less distorted (e.g., slanted aspects of an object may not appear to have wavy edges) relative to images produced from segments that are independent of the image plane. Further, computation time may be reduced (relative to the computation time that it presently takes to generate two-dimensional projection images from helical data) because less than all of a view is processed (e.g. only extracted segments of respective views are processed).

Moreover, the words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method for generating a two-dimensional (2D) image from a three-dimensional (3D) examination of an object, comprising:

determining an image plane for the 2D image;

setting an examination line, the examination line lying within a first plane substantially parallel to the image plane;

selecting, from a first view of the object, first data substantially indicative of a first ray passing through and perpendicular to the examination line, the selecting first data comprising:

extracting, from the first view, data yielded from two or more channels; and interpolating the data yielded from the two or more channels to generate the first data;

selecting, from a second view of the object, second data substantially indicative of a second ray passing through and perpendicular to the examination line; and generating the 2D image of the object using the first data and the second data.

2. The method of claim 1, the generating the 2D image, comprising:

using the first data and the second data to generate a projection line corresponding to the image plane; and using the projection line to generate the 2D image.

3. The method of claim 1, wherein the object under examination is helically scanned.

4. The method of claim 3, wherein the object under examination is helically scanned by a CT scanner.

5. The method of claim 1, wherein the first view is a cone view.

6. The method of claim 1, comprising:

determining a projection angle of the first ray and a cone angle of the first ray, wherein the selecting first data is based upon the projection angle and the cone angle.

7. The method of claim 1, wherein the examination line extends along an axis substantially perpendicular to an iso-center of an imaging system performing the 3D examination.

8. The method of claim 1, wherein the image plane is substantially parallel to an examination surface of a support article upon which the object resides during the 3D examination.

9. An apparatus for generating a two-dimensional (2D) image from a three-dimensional (3D) examination of an object, comprising:

a data extraction component configured to:
determine an image plane for the 2D image,
set an examination line, the examination line lying within a first plane substantially parallel to the image plane, and
extract a first segment of data from a first view of the object and extract a
second segment of data from a second view of the object, the first segment of data corresponding to a first ray passing through the examination line at a substantially perpendicular angle and the second segment of data corresponding to a second ray passing through the examination line at a substantially perpendicular angle;

a rebinner configured to:
interpolate the first segment of data to generate a first interpolated segment of data, and rebin the first interpolated segment of data with a second interpolated segment of data yielded from the second segment of data to generate a projection line; and an image reconstructor configured to reconstruct the 2D image using the projection line.

10. The apparatus of claim 9, comprising an ionizing radiation source configured to emit the first ray and the second ray.

11. The apparatus of claim 10, comprising a detector array configured to detect the first ray and the second ray.

12. The apparatus of claim 11, wherein a relative position between the ionizing radiation source and the detector array is maintained during the 3D examination.

13. The apparatus of claim 9, wherein the data extraction component is configured to determine a projection angle of the first ray and a cone angle of the first ray, and to extract the first segment of data based upon the projection angle and the cone angle.

14. The apparatus of claim 9, wherein the image plane is substantially parallel to an examination surface of a support article upon which the object resides during the 3D examination.

15. The apparatus of claim 9, wherein the examination line extends-along an axis substantially perpendicular to an iso-center of an imaging system performing the 3D examination.

16. A computer readable medium comprising computer readable instructions that when executed via a processor perform a method for generating a two-dimensional (2D) image from a three-dimensional (3D) examination of an object, the method comprising:

determining an image plane for the 2D image;

setting an examination line, the examination line lying within a first plane substantially parallel to the image plane;

identifying first data from a first view of the object substantially indicative of a first ray passing through and perpendicular to the examination line, comprising:

determining a projection angle of the first ray and a cone angle of the first ray; and selecting data yielded from one or more channels of a detector array where the first ray would intersect the detector array based upon the projection angle and the cone angle;

identifying second data from a second view of the object substantially indicative of a second ray passing through and perpendicular to the examination line; and generating the 2D image of the object using the first data and the second data.

17. The computer readable medium of claim 16, wherein the examination line is substantially perpendicular to an iso-center of an imaging system performing the 3D examination.

18. The computer readable medium of claim 16, wherein the 3D examination is performed by a CT scanner.

19. The computer readable medium of claim 16, comprising helically scanning the object during the 3D examination.

20. The computer readable medium of claim 16, wherein at least one of the first view or the second view comprises a cone view of the object.

* * * * *